United States Patent [19]
Mittelstadt

[11] Patent Number: 5,806,518
[45] Date of Patent: Sep. 15, 1998

[54] METHOD AND SYSTEM FOR POSITIONING SURGICAL ROBOT

[75] Inventor: Brent D. Mittelstadt, Placerville, Calif.

[73] Assignee: Integrated Surgical Systems, Sacramento, Calif.

[21] Appl. No.: 526,826

[22] Filed: Sep. 11, 1995

[51] Int. Cl.$^6$ .............................. B23Q 15/14; A61B 17/00
[52] U.S. Cl. ...................... 128/653.1; 128/920; 128/922; 395/80; 395/86; 901/30
[58] Field of Search ................................ 128/653.1, 782, 128/897, 898; 364/413.02, 413.13, 413.14; 606/130, 86, 89, 95, 60, 62, 63; 623/16, 22, 23; 395/80, 86, 89, 94, 924; 901/2, 30, 50

[56] References Cited

U.S. PATENT DOCUMENTS

| | | | |
|---|---|---|---|
| 5,086,401 | 2/1992 | Glassman et al. | 395/94 |
| 5,198,877 | 3/1993 | Schulz | 356/375 |
| 5,236,432 | 8/1993 | Matsen, III et al. | 606/88 |
| 5,249,581 | 10/1993 | Horbal et al. | |
| 5,299,288 | 3/1994 | Glassman et al. | 395/80 |
| 5,306,306 | 4/1994 | Bisek et al. | 623/16 |
| 5,320,115 | 6/1994 | Kenna | 128/898 |
| 5,343,877 | 9/1994 | Park | 128/898 |
| 5,383,454 | 1/1995 | Bucholz | 128/653.1 |
| 5,408,409 | 4/1995 | Glassman et al. | |
| 5,411,503 | 5/1995 | Hollstien et al. | |
| 5,480,400 | 1/1996 | Berger | |
| 5,524,180 | 6/1996 | Wang et al. | |
| 5,546,942 | 8/1996 | Zhang | |
| 5,564,437 | 10/1996 | Bainville et al. | |

FOREIGN PATENT DOCUMENTS

WO 91/07726  5/1991  WIPO .............................. G06F 15/72

OTHER PUBLICATIONS

Kazanzides, P., Zuhars, J., Mittelstadt, B.D., Taylor, R.H.: "Force Sensing and Control for a Surgical Robot," *Proc. IEEE Conference. on Robotics & Automation*, pp. 612–616, Nice, France, May 1992.

Kazanides, P., Zuhars, J., Mittelstadt, B.D., Williamson, B., Cain, P., Smith, F., Rose, L., Mustis, B.: "Architecture of a Surgical Robot," *Proc. IEEE Conference. on Systems, Man, and Cybernetics*, Chicago, Illinois, pp. 1624–1629, Oct., 1992.

Paul, H.A., Bargar, W.L., Mittelstadt, B., Musits, B., Taylor, R.H., Kazanzides, P., Zuhars, J., Williamson, B., Hanson, W.: "Development of a Surgical Robot For Cementless Total Hip Arthroplasty," *Clinical Orthopaedics*, vol. 285, pp. 57–66, Dec. 1992.

Kazanzides, P., Mittelstadt, B.D., Zuhars, J., Cain, P., Paul, H.A., "Surgical and Industrial Robots: Comparison and Case Study," *Proc. International Robots and Vision Automation Conference*, pp. 1019–1026, Detroit, Michigan, Apr. 1993.

Mittelstadt, B., Kazanzides, P., Zuhars, J., Williamson, B., Pettit, R., Cain, P., Kloth, D., Rose, L., Musits, B.: "Development of a surgical robot for cementless total hip replacement," *Robotica*, vol. 11, pp. 553–560, 1993.

(List continued on next page.)

*Primary Examiner*—Marvin M. Lateef
*Assistant Examiner*—Shawna J. Shaw

[57] ABSTRACT

A method for transforming the image of a long bone into a system coordinate space, such as robotic system coordinate space, comprises identifying in the image data set directional coordinates representing bone axis and at least one positional coordinate on the bone surface. Corresponding coordinates in the actual bone immobilized in the robotic or other system space are then determined by contacting a probe, such as a probe at the end of a manipulatable arm on a robot, to corresponding locations in the actual bone. The coordinates within the image data set are then registered with the actual coordinates within the immobilized bone to produce a transfer function that can be used to transform the image data set to the coordinate system space.

36 Claims, 8 Drawing Sheets

OTHER PUBLICATIONS

Mittelstadt B., Kazanzides, P., Zuhars, J., Cain, P., Williamson, B.: "Robotic surgery: Achieving predictable results in an unpredictable environment," *Proc. Sixth International Conference on Advanced Robotics*, pp. 367–372, Tokyo, Nov., 1993.

Cain, P., Kazanzides, P., Zuhars, J., Mittelstadt, B., Paul, H.: "Safety Considerations in a Surgical Robot," *Biomedical Sciences Instrumentation*, vol. 29, pp. 291–294, San Antonio, Texas, Apr. 1993.

Mittelstadt, B.D., Kazanzides, P., Zuhars, J., Williamson, B., Cain, P., Smith, F. Bargar, W.: "The Evolution of A Surgical Robot From Prototype to Human Clinical Use," *in Proc. First International Symposium on Medical Robotics and Computer Assisted Surgery*, vol. I, pp. 36–41, Pittsburgh, Pennsylvania, Sep. 1994.

Grimson, W.E.L., Lozano–Pérez, T. Wells III, W.M., Ettinger, G.J., White, S.J., Kikinis, R.: "Automated Registration for Enhanced Reality Visualization in Surgery," *Proceedings of the First International Symposium on Medical Robotics and Computer Assisted Surgery*, vol. I, Sessions I–III, pp. 82–89, Pittsburgh, Pennsylvania, Sep. 22–24, 1995.

Nolte, L.P., Zamorano, L.J., Jiang, Z., Wang, Q., Langlotz, F., Arm, E., Visarius, H.: "A Novel Approach to Computer Assisted Spine Surgery," *Proceedings of the First International Symposium on Medical Robotics and Computer Assisted Surgery*, vol. II, Sessions IV, pp. 315–321, Pittsburgh, Pennsylvania, Sep. 22–24, 1994.

Lavallée, S., Sautot, P., Troccaz, J., Cinquin, P., Merloz, P.: "Computer Assisted Spine Surgery: a technique for accurate transpedicular screw fixation using CT data and a 3–D optical localizer," *Proceedings of the First International Symposium on Medical Robotics and Computer Assisted Surgery*, vol. II, Session IV, pp. 315–321, Pittsburgh, Pennsylvania, Sep. 22–24, 1994.

Potamianos, P., Davies, B.L., Hibberd, R.D.: "Intra–Operative Imaging Guidance For Keyhole Surgery Methodology and Calibration," *Proceedings of the First International Symposium on Medical Robotics and Computer Assisted Surgery*, vol. I, sessions I–III, pp. 98–104, Pittsburgh, Pennsylvania, Sep. 22–224, 1994.

Simon, D.A., Herbert, M., Kanade, T.: "Techniques for Fast and Accurate Intra–Surgical Registration," *Proceedings of the First International Symposium on Medical Robotics and Computer Assisted Surgery*, vol. I, Sessions I–III, pp. 90–97, Pittsburgh, Pennsylvania, Sep. 22, 1995.

Péria, O., François–Joubert, A., Lavallée, S., Champleboux, L., Cinquin, P., Grand, S.: "Accurate Registration of SPECT and MR brain images of patients suffering from epilepsy or tumor," *Proceedings of the First International Symposium on Medical Robotics and Computer Assisted Surgery*, vol. II Session IV, pp. 58–62, Pittsburgh, Pennsylvania, Sep. 22–24, 1995.

Lea, J.T., Watkins, D., Mills, A., Peshkin, M.A., Kienzle III, T.C., Stulberg, D.S.: "Registration and Immobilization for Robot–Assisted Orthopaedic Surgery," *Proceedings of the First International Symposium on Medical Robotics and Computer Assisted Surgery*, vol. I, Sessions I–III, pp. 63–63, Pittsburgh, Pennsylvania, Sep. 22–24, 1995.

Ault, T., Siegel, M.W.: "Frameless Patient Registration Using Ultrasonic Imaging," *Proceedings of the First International Symposium on Medical Robotics and Computer Assisted Surgery*, vol. I, Sessions I–III, pp. 74–81, Pittsburgh, Pennsylvania, Sep. 22–24, 1995.

Champleboux, G., Lavallée, S., Cinquin, P.: "An Optical Conformer for Radiotherapy Treatment Planning," *Proceedings of the First International Symposium on Medical Robotics and Computer Assisted Surgery*, vol. I, Sessions I–III, pp. 69–73, Pittsburgh, Pennsylvania, Sep. 22–24, 1995.

METHOD AND SYSTEM FOR POSITIONING SURGICAL ROBOT

BACKGROUND OF THE INVENTION

1. Field of the Invention

The present invention relates generally to surgical methods and systems. More particularly, the present invention relates to a method and system for registering the position of a robotically manipulated surgical tool with a preoperative image of a long bone.

Robotic systems for assisting in a number of medical procedures have been proposed, including neurosurgical, laparoscopic, and orthopedic procedures. While the details of a particular procedure may vary widely, a number of such procedures rely on first obtaining a preoperative image of the region to be operated on, and subsequently robotically controlling a medical tool based on information in the preoperative image. The procedures are usually surgical but can also be diagnostic. A need thus exists for transforming the preoperative image (usually in the form of a digital data set obtained by conventional imaging techniques) to a coordinate system employed by the robot. In this way, the robot is able to navigate the surgical tool based on the image data set which is representative of the patient's actual anatomy.

Of particular interest to the present invention, robotically assisted total hip replacement surgery is performed by first imaging the femur, typically by computerized tomography (CT), and producing a digital data set representative of the femur. Selection and positioning of an implant within the femur is then planned at a computer workstation, such as the ORTHODOC™ presurgical planning workstation being developed by Integrated Surgical Systems, Inc., Sacramento, Calif., assignee of the present application. Once the doctor has planned the implant placement on the workstation, a digital data set including both the image data (patient anatomy) and the planned positioning of the implant is produced. It is then necessary to transfer this data set to a computer-controlled robotic system intended to perform the surgery, such as the ROBODOC™ surgical robot system which is also being developed by Integrated Surgical Systems.

Successful hip replacement surgery, particularly when using cementless implants, relies on the highly accurate creation of a cavity within the proximal (upper) end of the femur for receiving the implant. Deviations less than ±1 mm from the planned cavity placement are desirable. A critical requirement in achieving such accuracy is precise registration between the image data set and the coordinate system of the surgical robot.

Image registration within the robotic coordinate system requires correlation between the physical position of the patient body site to be operated on, e.g., the femur in total hip replacement and knee replacement procedures, the digital image set representing the body feature, and the robotic coordinate system. Such correlation may be achieved by registering the image data set with the actual position of the body feature within the robotic coordinate space by physically contacting a probe at the end of a manipulator arm of the robot against certain imaged features on the body part. The information thus obtained by the robot controller can then be used to register the image with the actual body site, e.g., an immobilized femur, within the operative space of the robot. In particular, the ROBODOC™ surgical robot system relies on the surgical implantation of a pair of metallic pins on the distal (lower) end of the femur and one additional metallic pin in the proximal end of the bone. These pins are readily apparent in the CT image of the bone and can thus be relied on to register the bone image with the robotic coordinate space by engaging a probe placed on the manipulator arm against each of the pins. Such registration is described in detail in Taylor et al. (1994) IEEE Trans. Robotics Automat. 10:261–275.

While capable of achieving a high degree of accuracy and precision, the use of pins requires an additional surgical procedure for implantation. Moreover, the need to implant pins at the distal end of the femur requires surgical access to a site which might otherwise be left intact. The need to perform the additional procedure increases the time, cost, and patient discomfort associated with the total hip replacement procedure to a significant extent.

For these reasons, it would be desirable to provide improved methods in robotic systems for performing surgical procedures on long bones, such as joint replacement procedures on femurs and other long bones. It would be particularly desirable to provide methods and systems for transforming a preoperative image of the bone and operative plan to a robotic coordinate system without the need to rely on access to a remote portion of the bone which need not otherwise be accessed. It would be particularly desirable if such procedures could dispense with the use of marker pins altogether, although procedures which relied on one or more marker pins at the proximal end of the bone which would normally be accessed during the replacement surgery would also be beneficial.

2. Description of the Background Art

The ORTHODOC™ presurgical planning workstation and the ROBODOC™ robotic surgical system are described in a number of references, including the following: (1) Kazanzides, P., Zuhars, J., Mittelstadt, B. D., Taylor, R. H.: "Force Sensing and Control for a Surgical Robot," *Proc. IEEE Conference. on Robotics & Automation,* Pages 612–616, Nice, France, May 1992. (2) Kazanzides, P., Zuhars, J., Mittelstadt, B. D., Williamson, B., Cain, P., Smith, F., Rose, L., Mustis, B.: "Architecture of a Surgical Robot," *Proc. IEEE Conference. on Systems, Man, and Cybernetics,* Chicago, Ill., Pages 1624–1629, October, 1992. (3) Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," *Clinical Orthopaedics,* Volume 285, Pages 57–66, December 1992. (4) Kazanzides, P., Mittelstadt, B. D., Zuhars, J., Cain, P., Paul, H. A., "Surgical and Industrial Robots: Comparison and Case Study," *Proc. International Robots and Vision Automation Conference,* Pages 1019–1026, Detroit, Mich., April 1993. (5) Mittelstadt, B., Kazanzides, P., Zuhars, J., Williamson, B., Pettit, R., Cain, P., Kloth, D., Rose, L., Musits, B.: "Development of a surgical robot for cementless total hip replacement," *Robotica,* Volume 11, Pages 553–560, 1993. (6) Mittelstadt B., Kazanzides, P., Zuhars, J., Cain, P., Williamson, B.: "Robotic surgery: Achieving predictable results in an unpredictable environment," *Proc. Sixth International Conference on Advanced Robotics,* Pages 367–372, Tokyo, November, 1993. (7) Cain, P., Kazanzides, P., Zuhars, J., Mittelstadt, B., Paul, H.: "Safety Considerations in a Surgical Robot," *Biomedical Sciences Instrumentation,* Volume 29, Pages 291–294, San Antonio, Tex., April 1993. (8) Mittelstadt, B. D., Kazanzides, P., Zuhars, J., Williamson, B., Cain, P., Smith, F. Bargar, W.: "The Evolution of A Surgical Robot From Prototype to Human Clinical Use," in *Proc. First International Symposium on Medical Robotics and Computer Assisted Surgery,* Volume I, Pages 36–41, Pittsburgh, Pa., September 1994.

Other publications which describe image registration in robotic surgical and other procedures include the following: (9) Grimson, W. E. L., Lozano-Pérez, T., Wells III, W. M., Ettinger, G. J., White, S. J., Kikinis, R.: "Automated Registration for Enhanced Reality Visualization in Surgery," *Proceedings of the First International Symposium on Medical Robotics and Computer Assisted Surgery*, Volume I, Sessions I–III, Pages 82–89, Pittsburgh, Pa., Sep. 22–24, 1995. (10) Nolte, L. P., Zamorano, L. J., Jiang, Z., Wang, Q., Langlotz, F., Arm, E., Visarius, H.: "A Novel Approach to Computer Assisted Spine Surgery," *Proceedings of the First International Symposium on Medical Robotics and Computer Assisted Surgery*, Volume II, Session IV, Pages 323–328, Pittsburgh, Pa., Sep. 22–24, 1994. (11) Lavallée, S., Sautot, P., Troccaz, J., Cinquin, P., Merloz, P.: "Computer Assisted Spine Surgery: a technique for accurate transpedicular screw fixation using CT data and a 3-D optical localizer," *Proceedings of the First International Symposium on Medical Robotics and Computer Assisted Surgery*, Volume II, Session IV, Pages 315–321, Pittsburgh, Pa., Sep. 22–24, 1994. (12) Potamianos, P., Davies, B. L., Hibberd, R. D.: "Intra-Operative Imaging Guidance For Keyhole Surgery Methodology and Calibration," *Proceedings of the First International Symposium on Medical Robotics and Computer Assisted Surgery*, Volume I, Sessions I–III, Pages 98–104, Pittsburgh, Pa., Sep. 22–24, 1994. (13) Simon, D. A., Hebert, M., Kanade, T.: "Techniques for Fast and Accurate Intra-Surgical Registration," *Proceedings of the First International Symposium on Medical Robotics and Computer Assisted Surgery*, Volume I, Sessions I–III, Pages 90–97, Pittsburgh, Pa., Sep. 22–24, 1995. (14) Peria, O., François-Joubert, A., Lavallée, S., Champleboux, G., Cinquin, P., Grand, S.: "Accurate Registration of SPECT and MR brain images of patients suffering from epilepsy or tumor," *Proceedings of the First International Symposium on Medical Robotics and Computer Assisted Surgery*, Volume II, Session IV, Pages 58–62, Pittsburgh, Pa., Sep. 22–24, 1995. (15) Lea, J. T., Watkins, D., Mills, A., Peshkin, M. A., Kienzle III, T. C., Stulberg, D. S.: "Registration and Immobilization for Robot-Assisted Orthopaedic Surgery," *Proceedings of the First International Symposium on Medical Robotics and Computer Assisted Surgery*, Volume I, Sessions I–III, Pages 63–68, Pittsburgh, Pa., Sep. 22–24, 1995. (16) Ault, T., Siegel, M. W.: "Frameless Patient Registration Using Ultrasonic Imaging," *Proceedings of the First International Symposium on Medical Robotics and Computer Assisted Surgery*, Volume I, Sessions I–III, Pages 74–81, Pittsburgh, Pa., Sep. 22–24, 1995. (17) Champleboux, G., Lavallée, S., Cinquin, P.: "An Optical Conformer for Radiotherapy Treatment Planning," *Proceedings of the First International Symposium on Medical Robotics and Computer Assisted Surgery*, Volume I, Sessions I–III, Pages 69–73, Pittsburgh, Pa., Sep. 22–24, 1995.

A system and method for performing robotically assisted surgery is described in U.S. Pat. No. 5,086,401. Computer-assisted imaging and probe tracking systems are described in U.S. Pat. No. 5,383,454; U.S. Pat. No. 5,198,877; and WO 91/07726.

SUMMARY OF THE INVENTION

According to the present invention, improved methods, systems and apparatus are provided for registering the image of a long bone with the bone itself immobilized in a coordinate system, typically a robotic coordinate system of the type used for performing surgical procedures, such as hip replacement surgery, knee replacement surgery, long bone osteotomies, and the like. The improvement comprises registering an image data set with the robotic or other coordinate system based on a correlation between (1) directional coordinates representing the bone axis and (2) at least one positional coordinate on the bone surface. The image data set is obtained in a presurgical imaging procedure, such as computerized tomography (CT), digital radiography, or the like. Locations representative of the bone axis are identified by a user reviewing the image, typically by marking a plurality of center points along the medullary canal in the bone image or automatically by the system software. In addition, at least one point on the bone surface is also marked by the user on the image data set, typically a plurality of marks representing a surface region on the bone are marked, or automatically identified by the system. The corresponding locations in the actual bone are then located while the bone is immobilized in the robotic or other system which defines the system coordinates. A system controller then transforms the image data set to the robotic coordinate system by registering the axial and positional coordinates in the image coordinate system with those in the system coordinate system.

The methods, systems, and apparatus of the present invention are particularly advantageous since they provide for a very accurate registration of the image data set to the actual bone position when immobilized in the coordinate system. It has been found that a combination of the axial coordinates with the surface coordinate(s) provides for registration within a tolerance of less than ±2 mm, usually less than ±1 mm, and preferably less than ±0.5 mm. Such tolerances allow even cementless positioning of hip joint implants with good initial mechanical stability and excellent tissue ingrowth. Moreover, the methods, systems, and apparatus of the present invention obviate the need to implant a plurality of bone surface markers prior to the actual implant surgery. Even when the bone marker is utilized in the upper end of the bone (which is an option in the method of the present invention), there is no need to implant additional markers at the lower end of the bone, e.g., the distal end of the femur in hip replacement surgery.

In a first specific aspect of the method of the present invention, the long bone is immobilized in a workspace of a mechanical manipulator having an effector or probe positionable in a coordinate system. The effector is translated through the medullary canal of the bone to acquire axial coordinates. The probe is also contacted against the surface of the bone to acquire at least one surface positional coordinate. The data set representing an image of the bone and having predefined axial and positional coordinates may then be transformed into the system coordinates by registering the corresponding axial and positional coordinates between the image and the immobilized bone. Typically, the medullary canal will be surgically accessed from one end of the bone and cleared in order to receive the probe. The probe is then introduced through the access hole, and its distal end is centered at various axial positions along the bone. Centering is typically accomplished by inflating a centering balloon near the distal end of the probe and force-balancing the probe. The manipulator system then records the center positions along the medullary canal as defined in system coordinates. Similarly, the probe is contacted against one or more surface locations on the bone, typically in the proximal calcar region of the femur for hip replacement. The image is then registered with analogous positions which have been marked in the image data set by the user. Transforming the data set is typically accomplished by generating a transform function which can transform the image data set into the coordinate system of the manipulator system.

The method may further comprise obtaining the image data set. Typically, the image data set is obtained by providing a raw image data set of the bone, typically acquired by any of the imaging techniques described above. The user selects and marks a plurality of coordinates along a center line through the image of the medullary canal. For example, this can be done by centering elliptical templates over cross-sectional images of the bone to define the center points. Additionally, the user will generate a surface model representing a region near one end of the bone, typically in the proximal calcar region of the femur for hip replacement. These locations are then stored within the image data set and relied on for registering the image data set with the actual position of the immobilized bone within the robotic or other system. Alternatively, the system software can determine the centerline and surface coordinates automatically.

In a second aspect of the method of the present invention, hip replacement surgery may be performed by positioning a surgical cutter based on information in a transformed image data set obtained by any of the methods described above. The cutter is positioned according to a preoperative plan, and the cutter is actuated to produce a cavity for receiving a hip joint replacement prosthesis. The hip joint replacement prosthesis is then implanted in the cavity.

The present invention still further provides an improved robotic system of the type having a manipulable arm which carries a surgical cutter. The system further includes a programmable controller which positions the cutter within a robotic coordinating system. An image data set representing the image of a long bone is transformed to the robotic coordinate system to permit the controller to position the cutter according to a predetermined operative plan. The improvement comprises a system controller which transforms the image data set to the robotic coordinate system by registering (1) directional coordinates representing the bone axis and (2) at least one positional coordinate on the bone surface.

The present invention still further provides an improved robotic system of the type having a manipulatable effector and a positioning probe removably attached to the effector. The improvement comprises a probe having an expansible element, such as an inflatable cuff, lined centering cone (umbrella structure), or the like, for centering the probe within a lumenal space and an actuator for expanding the element while the probe is positioned within the lumenal space. Such robotic system may be used in the image transforming methods described above.

The present invention still further provides a positioning probe for use with a robotic system having a manipulatable effector. The probe comprises a rigid probe body having a proximal and a distal end. The connector is disposed at the proximal end of the probe and is removably connected thereto. An expansible element on the probe body permits the probe to be centered within a lumenal space. The positioning probe is particularly useful in the image transforming methods described above.

DESCRIPTION OF THE SPECIFIC EMBODIMENTS

The present invention is intended for registering the image of the long bone with the long bone itself immobilized within a system coordinate space. Long bones which may be imaged and registered include the femur, tibia, humerus, ulna, and radius. Image registration of such long bones will be particularly useful in conjunction with robotic surgical procedures, such as joint replacement, with specific procedures including total hip joint replacement, knee joint replacement, long bone osteotomy, and the like. Exemplary methods, systems, and apparatus for transforming an image data set of the femur within a robotic system intended for performing total hip replacement surgery are described hereinafter, but such descriptions are not intended to be limiting to the scope of the present invention.

The present invention provides methods, systems, apparatus for transforming the image data set of the long bone to a system coordinate space, typically a robotic system intended to perform or assist in any of the procedures described above. The present invention, however, is not limited to such robotic procedures and will be equally useful in manual surgical, diagnostic, and other medical procedures where it is necessary to align a pre-obtained image of a long bone within an actual coordinate space, such as an operative space. Such manual systems and procedures include computer-assisted surgical procedures that employ optical surgical measurement tools, passive electromechanical devices, and the like. In such cases, the use of the present invention is advantageous in that it will provide highly accurate image registration with an immobilized long bone without the need to preimplant multiple markers along the bone and/or surgically access the bone at multiple points along its length.

The present invention relies on obtaining an image of the bone using a conventional medical imaging technique, such as computerized tomography (CT), radiography (digitized X-ray images), magnetic resonance imaging (MRI), and the like. Usually, CT and radiographic imaging will be preferred since they provide particularly accurate imaging information of bone material. In all cases, the image will be obtained in or converted to a digital form to produce an image data set which is suitable for digital manipulation using conventional computerized image processing equipment and software. Usually, the image processing equipment will be in the form of specially programmed computers, which are generally referred to as controllers and processors hereinafter. In particular, the present invention will utilize a preoperative planning work station (computer) for analyzing and manipulating raw image data which is obtained directly from the image itself. The raw image data set will be processed to include specific marker points or locations which are subsequently relied on to transform the image data set into the system coordinate space, as described in detail hereinafter. The marker locations may be identified by the user who views the image on the screen and marks particular locations on the image which are intended for alignment with the actual bone when the bone is immobilized in the system coordinate space. Alternatively, the preoperative planning workstation could be programmed to identify suitable marker locations without specific user intervention. In both cases, the marker locations will become part of the image data set which is subsequently transferred to the operative or other system in which the bone is to be immobilized.

The present invention relies particularly on obtaining axial and surface positional information on the bone and registering such information between the image data set and the system data set (representing the actual bone) as part of the image transformation process. In particular, center point data taken along the medullary canal in the image data set are obtained and compared to corresponding center points of the actual bone immobilized in the operative space. It will be appreciated that the medullary canal of the long bone will, in most cases, not be completely straight, and may vary from straightness by as much ±15 mm over a length of 20 cm. The center point data in both the image data set and the system data set will thus be non-linear and will require alignment by non-linear techniques, such as regression analysis. Usually, the center point data will be aligned by the robotic system at the same time as the surface data are aligned.

Surface positional information will comprise one or more points on the exterior surface of the bone, typically near the proximal end so that the distal end need not be surgically exposed. Usually, the surface information will be a surface model generated from the image data set, and the surface model will be aligned with at least one, and preferably at least three points determined by the robotic system within the robotic field. The surface data in the image data set will be aligned with the point(s) by regression analysis. The use of a fixed surface point, typically provided by a surgically preimplanted marker, can eliminate the need to fit multiple points with a surface model since a single, precisely located point will provide a high level of accuracy when combined with canal center line data according to the present invention.

A particular advantage of the present invention is the ability to transform the image data set without the need to surgically implant locating markers onto the bone. The ability to eliminate the markers derives largely from the use of the axial positional information which is obtained without the use of markers by the methods described in more detail below. Usually, the surface locational information of the bone will also be obtained without the use of markers. Optionally, one or more surface markers may be attached to the bone and used to provide surface information in combination with the axial information obtained without the use of surface markers. In particular, it has been found that use of single surface marker at one end of the long bone, typically at the head of the femur in hip replacement or the bottom of the femur in knee replacement, will provide sufficient surface information for performing the transformation of the present invention. In the exemplary embodiment, surface information is obtained in a plurality of positions over a surface region of the bone and the use of implanted markers is eliminated entirely.

Figure 1:
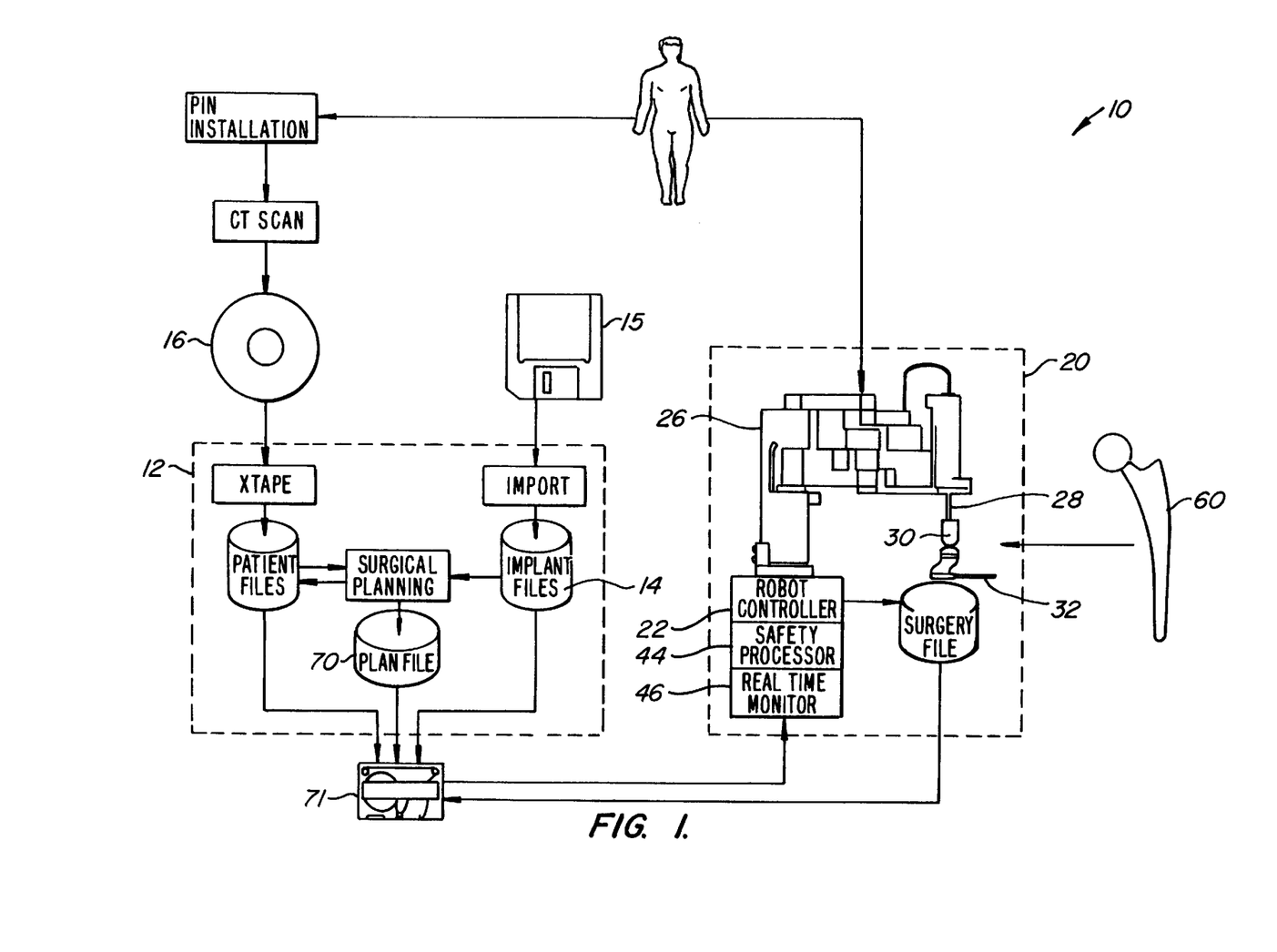
FIG. 1 illustrates the architecture of a robotic surgical system according to the present invention. The system includes a presurgical planning component and a surgical component.

An exemplary system 10 capable of implementing the methods of the present invention for hip replacement surgery is illustrated in FIG. 1. The system 10 includes both a presurgical planning workstation 12 and a library of implant designs 14 in the form of CAD models which are available from manufacturers on disks 15. A raw image data set 16, typically CT data, of the bone is obtained and transferred into the presurgical planning workstation 12. Optionally, a single pin may be implanted in the proximal femur for determining a surface data point. The user, typically the treating physician or an assistant working with the treating physician, is able to work at the presurgical planning workstation to select and position a suitable implant design within the patient femur. Details of such presurgical planning are well described in the literature relating to the ORTHODOC™ presurgical planning system cited above. In addition to the implant planning and data generation, the user will identify axial and surface coordinate positions in the raw image data which are relied to subsequently transform the image data set to the robotic coordinate system, as described in more detail below.

Figure 2:
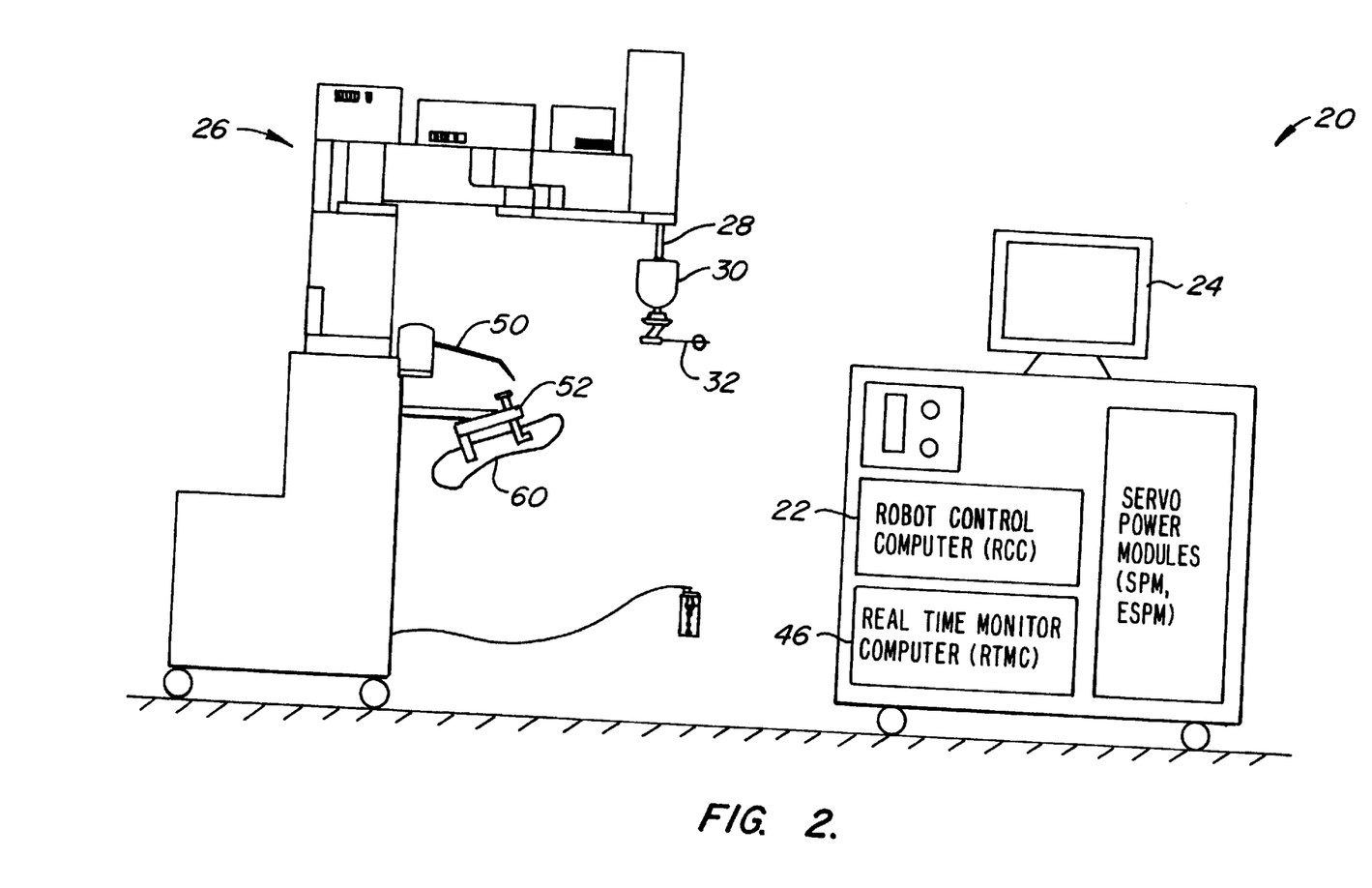
FIG. 2 illustrates the surgical component of the surgical system of FIG. 1 and includes the surgical robot with its associated controller, tooling, and safety interlocks, a fixator to hold the bone securely to the robot, a bone motion detector, a human-machine interface with online display computer, and a hand-held terminal interfaced to the robot controller.

The system 10 of the present invention further comprises a robotic operative system 20 which includes a robotic controller 22 (typically a digital processor in the form of a programmable computer), an online display screen 24, and a robot 26. Details of the robotic operating system 20 are shown in FIG. 2. The robot can be any conventional industrial robot having a manipulatable arm 28 preferably having at least 5 axes and capable of high precision placement. A suitable robotic is available from Sankyo Robotics with the model designation SR-5427-ISS. For use in the present invention, a force sensor 30 is mounted at the distal end of arm 28, and an effector in the form of a probe 32 or a surgical cutting tool (not illustrated) may be attached to the force sensor.

The robotic system 20 further includes a safety processor 44, and a real time monitoring computer 46, as illustrated in FIG. 1. The force sensor 30, the safety processor 44, the real time monitor 46, and a bone motion monitor 50, each help monitor the position, slippage, and blockage of the effector end of the manipulatable arm 28 while the femur 60 is held in place in a fixator assembly 52. Real time monitoring of these parameters helps assure that the robotic system is operating as planned. Details of these monitoring systems are described in the literature cited above which describes the ROBODOC™ robotic surgical system.

As described to this point, the system 10 architecture and the preoperative planning work station 12 and robotic operative system 20 are generally conventional. In order to practice the present invention, these systems must be modified as described hereinafter.

Figure 3:
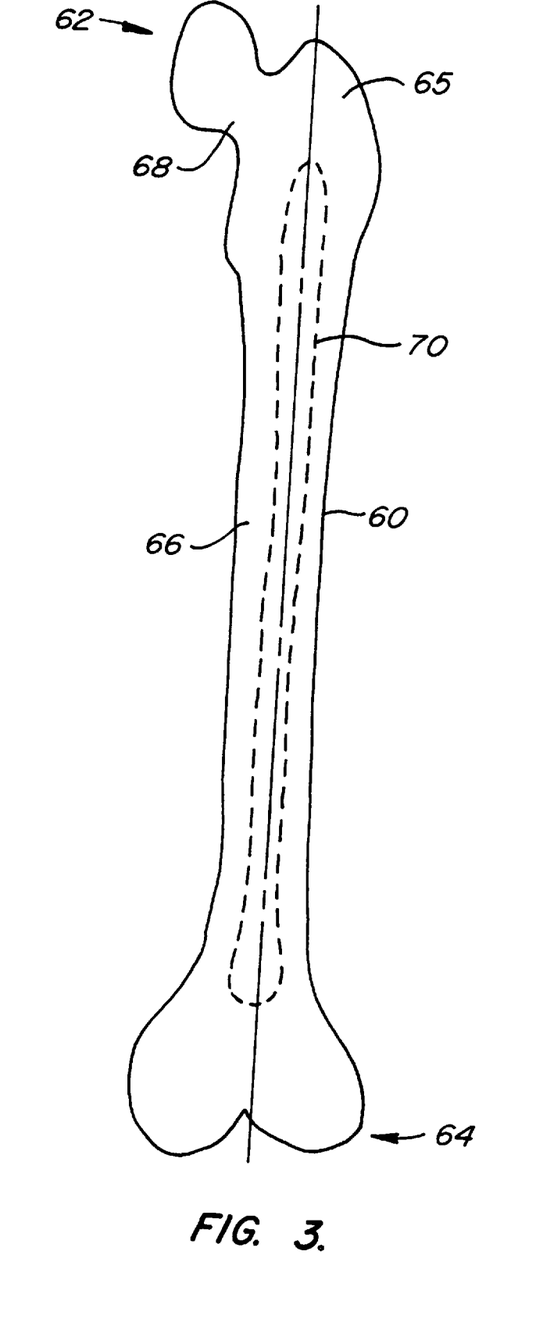
FIG. 3 is a schematic illustration of a human femur.
Figure 4:
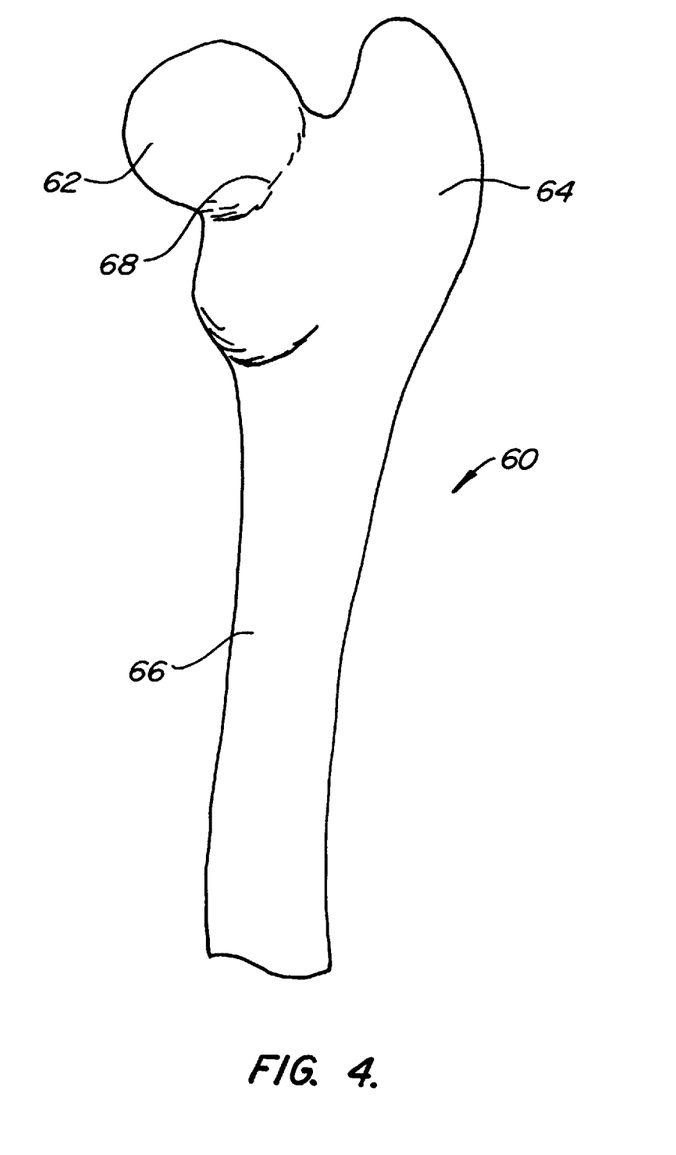
FIG. 4 is a detailed view of the upper end of a human femur.

Before describing the system modifications in detail, however, it is necessary to describe the physical characteristics of the femur, a typical long bone. Referring now to FIGS. 3 and 4, a femur 60 comprises a head region 62 and a lower region 64. The trabecular bone 65 that is located adjacent the femoral head 62 and the cortical bone is located generally between the two ends of the bone. A neck region 68 is located just below the femoral head above the trabecular bone. Finally, the medullary canal 70 runs generally axially through the cortical bone region of the femur, as shown in broken line.

The specific details of the preoperative planning component of the method of the present invention will now be described in more detail. After the user completes the preoperative plan including selection and positioning of a suitable implant prosthesis, the preoperative planning workstation 12 will produce a plurality of cross-sectional images on the viewing screen. The image data will delineate the periphery of the medullary canal of the long bone. Typically, from two to eight cross-sections will be produced, but in some cases it may be desirable to produce 12, 16, or even more images. The axial distances of each cross-section from the selected position of the implant tip are known.

The user then identifies a center point in each of the cross-sectional images. Such selection could be done subjectively, i.e., by positioning a screen marker visually within the periphery of the medullary canal and marking the position in the image data set when it is selected. Preferably, the system will produce elliptical templates which the user may position and size within each cross-sectional image. In particular, the elliptical templates can be rotated about their elliptical center and sized in both the major and minor diameters in order to match the periphery of the medullary canal as closely as possible. The system can then mark and store the center of the ellipse as the center of the medullary canal at that cross-sectional location. Alternatively, the system could be programmed to generate such cross-sectional information automatically, without specific user intervention. In either case, the center points are made part of the image data set and transferred to the robotic system 20. The image center points will then be aligned with actual canal center points (collected as described below) to provide for axial alignment of the image and the immobilized bone.

In addition to obtaining bone canal center data points, as just described, at least one surface locational point will be identified within the image data set within the preoperative planning workstation 12. This could be done in a variety of ways. For example, the user could identify one or more specific locations on the exterior surface of the bone and mark them for storage within the image data set. Alternatively, a single data point could be relied on if a marker had been surgically preimplanted in the bone prior to imaging. In that case, the preoperative planning workstation could automatically identify the marker without intervention by the user. In the exemplary embodiment, the workstation 12 will generate a surface model of a portion of the exterior of the bone, usually representing the outer cortex and the proximal calcar region. The particular boundaries for the region may be determined by the user or may be calculated by the workstation 12 based on the implant placement which in turn determines the level of which the femoral head will be excised. While it would be possible to generate a surface model of the entire bone, it has been found that use of a small portion of the proximal calcar region is sufficient to provide accurate image registration without excessive computational time. The image data set, including the identified positional coordinates, is then transferred to the robotic operative system 20 as part of a data transfer file 70 including the image information, implant shape data, and implant placement data. Transfer is conveniently accomplished via a transfer tape 71, but could be done using any conventional data transfer methodology. Additionally, the three-dimensional models of the bone and implant (implant files 14) are also transferred to the online display 24 of the robotic system 20 via the tape 71.

Figure 5:
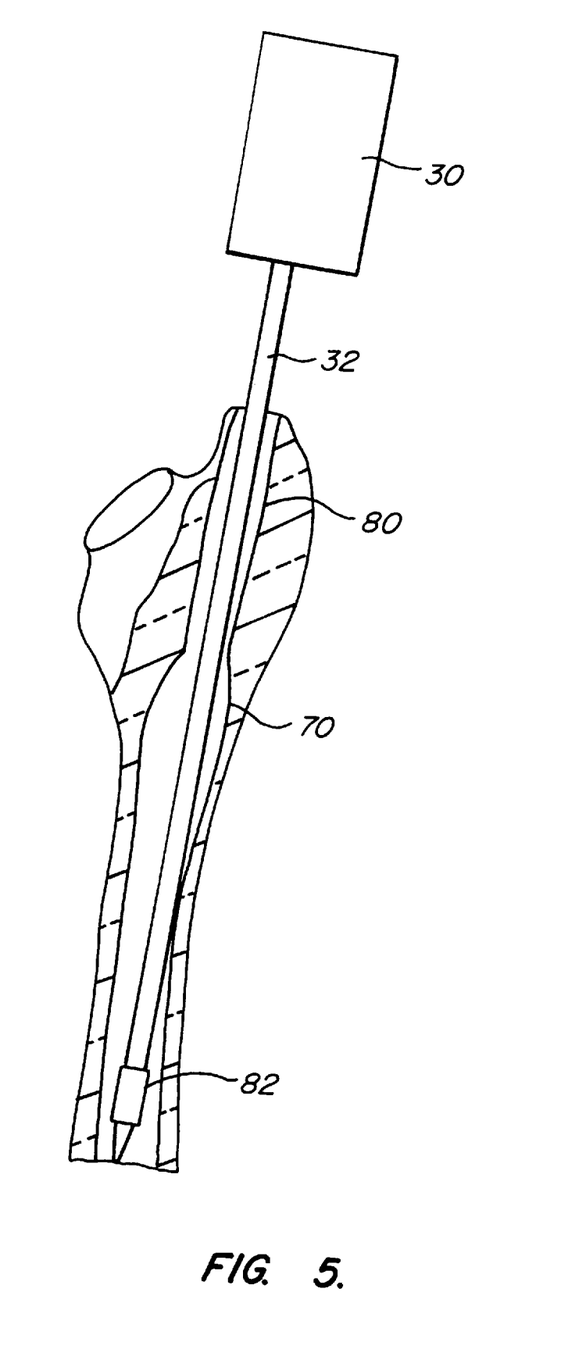
FIGS. 5–7 illustrate the use of a robotic probe for gathering axial center line data in the medullar canal of a human femur according to the method of the present invention.
Figure 6:
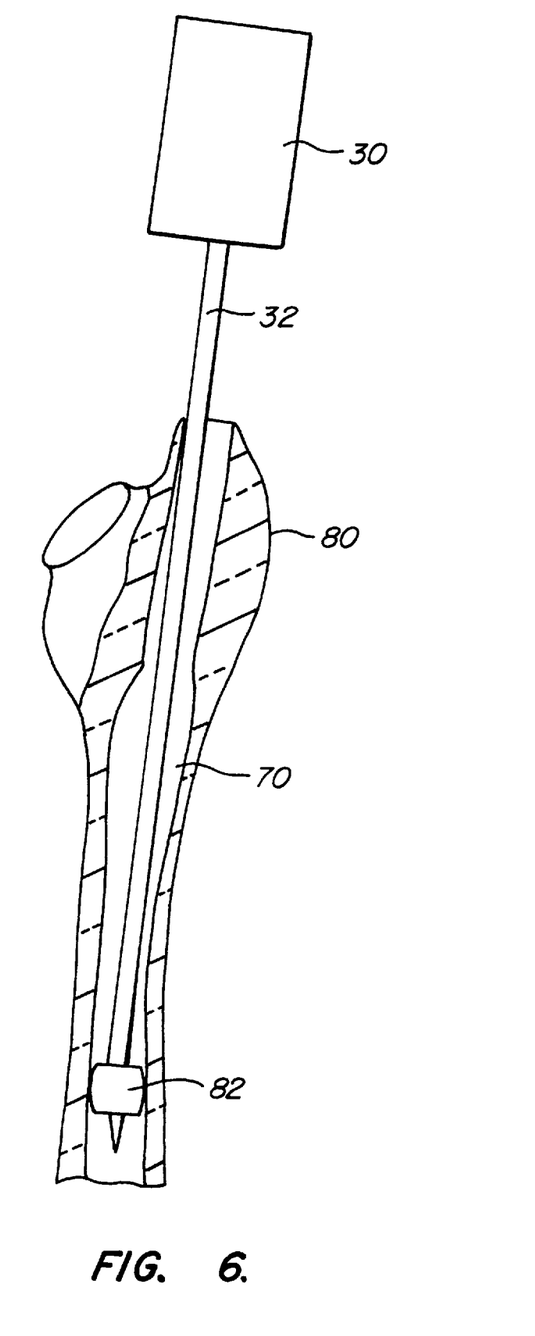
Figure 7:
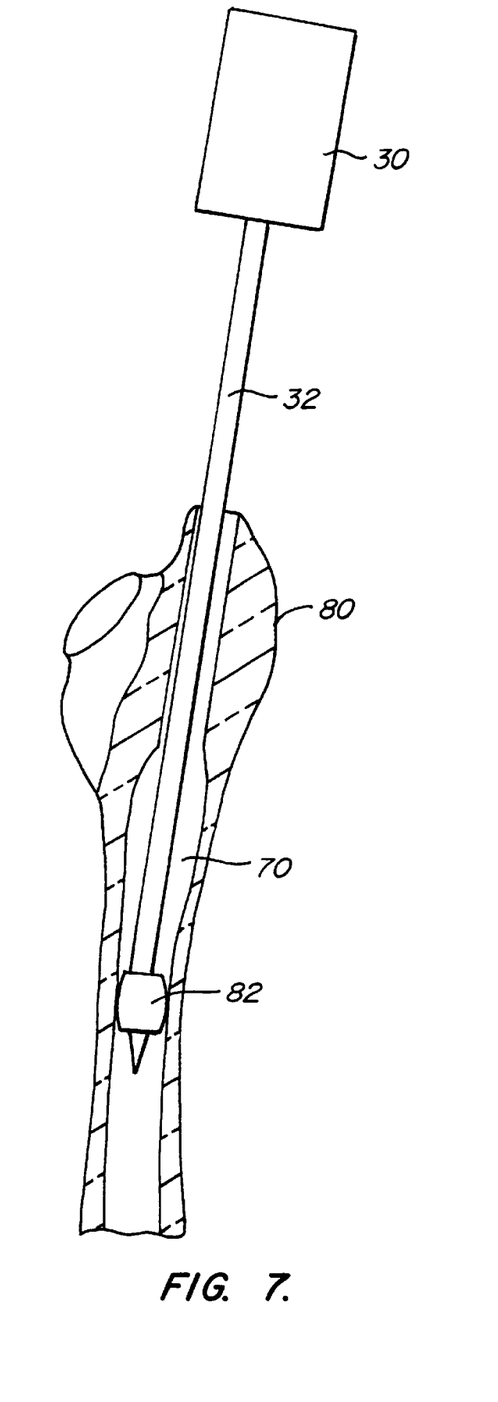

The robotic operative system 20 is then operated to obtain positional information on the bone when the bone is immobilized within the robotic system. The patient will be prepared for hip replacement surgery in a conventional manner, and will be immobilized within the robotic operative system 20 generally as described in the literature related to the ROBODOC™ robotic operative system set forth above. The only unique aspects of the method of the present invention relate to the acquisition of positional information which is to be used for registration with the positional information acquired as described above and incorporated into the image data set transferred to the robotic operative system 20. As described in FIGS. 5–7, the probe 32 as utilized to obtain canal center line information through the medullary canal 70. Initially, the surgeon performs a femoral head osteotomy and prepares the acetabulum in a conventional manner, except that the depth of the osteotomy may be at a higher level in order to retain more of the neck which includes the surface-model region of the bone. An access hole 80 is opened in the trabecular bone and the bone is then installed in the femoral fixator of the robotic operative system 20.

The probe 32 then introduced into the medullary canal 70 by manually guiding the probe. The ability to manually guide the probe and cause the manipulator arm 28 to follow is well described in the literature describing the ROBODOC™ robotic operative system. The probe 32 is positioned so that an expansible distal end, illustrated as an inflatable balloon, is sequentially aligned at least two axially spaced-apart positions within the canal corresponding to the axial positions which have been cross-sectionally imaged in the preoperative planning session. By expansion, the distal end of the probe will be automatically centered, and the robot is able to store the position of the probe with reference to the robot coordinate system within the robot controller. The balloon is then deflated (or other expansible end reduced in size) and moved to the at least second position, as shown FIG. 7, where it is reinflated. Typically, the probe will be located and centered at each of the cross-sectional locations which have been established during the preoperative planning procedure. Positional measurement of the probe will occur while the balloon is inflated and the robotic system is in a force-control mode that will move the probe tip in order to balance forces on the probe as sensed by the force sensor 30. The probe will be moved about the bone entry point, when the forces are balanced, the user will verify that the probe shaft is not contacting the proximal femur. Upon confirmation, the system will record the center point of the probe. This procedure is repeated at each level at which the center point location is determined.

Figure 8:
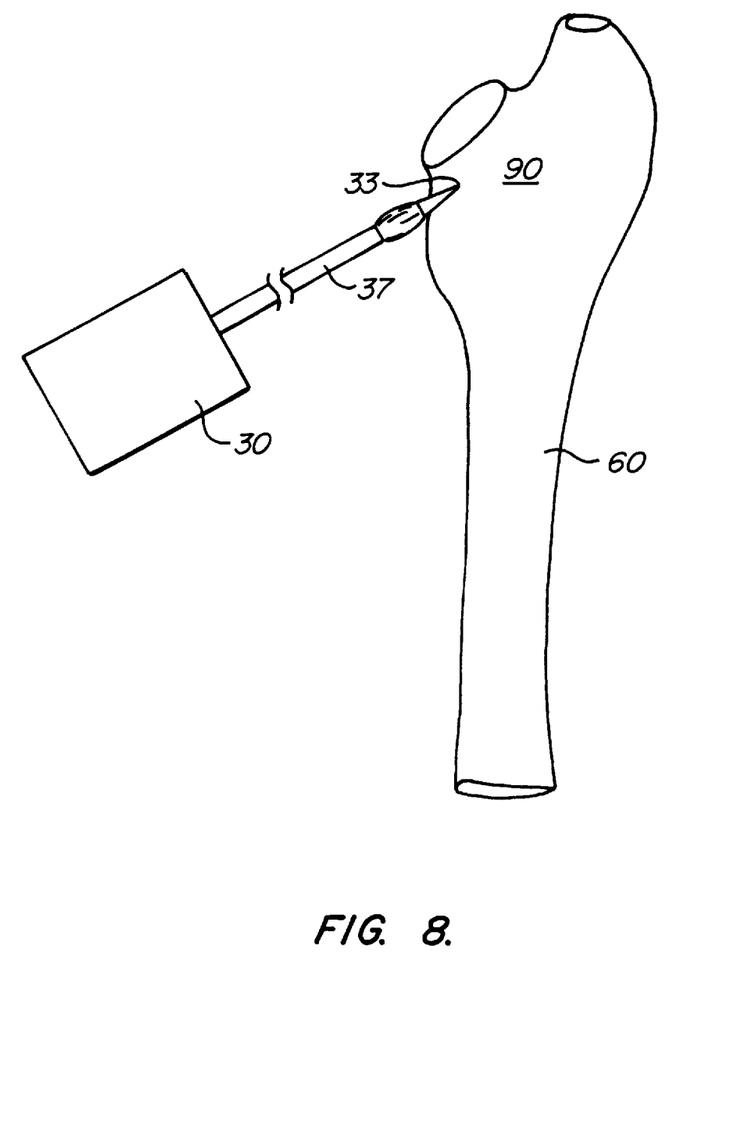
FIG. 8 illustrates the use of a robotic probe to gather surface positional information from a human femur according to the method of the present invention.

Referring now to FIG. 8, the probe 32 is used to collect surface locational information in the proximal calcar region 90 of the femur 60 as follows. Typically, the probe tip 33 will be engaged against at least one point on the anterior surface of the calcar region and one point on the posterior surface of the calcar region. The system will assure that the probe tip is force-balanced prior to recording the position in the robot controller. Optionally, a greater number of points, e.g., from 10 to 15 point, may be used in order to increase the accuracy of the transformation function which is produced.

The robot controller 22 now has sufficient information to generate a transformation function which can be used to transform the image data set into robotic coordinates. Thus, the image data set can be used to control the manipulator arm 28 of the robot for performing the desired surgical procedure, e.g., creation of an implant cavity for receiving the prosthetic hip implant, as generally described in the earlier ROBODOC™ publications. The transfer file 72 received from the presurgical planning workstation 12 will include the implant data, canal center point data, surface model of the femoral neck region in a suitable file format, and all other planning information necessary to operate the robotic system 20.

Once the robotic system 20 has both the image data set and the canal center point and surface positional information, transformation of the image data set to the robotic coordinate system can be achieved by conventional mathematical techniques. In the exemplary embodiment the canal center points are fit to the robotically determined center points by conventional regression analysis. Similarly, a plurality of robotically determined surface points are fit with the surface model, also by regression analysis. Once an optimum fit has been calculated, the robotic system 20 generates a transfer function which is used by the robotic system 10 to transform the image data set coordinates to the robotic coordinate system.

After the transformation function has been obtained the remainder of the surgical procedure for hip joint replacement can be performed generally as described in the literature relating to the ROBODOC™ robotic surgical system.

Although the foregoing invention has been described in some detail by way of illustration and example, for purposes of clarity of understanding, it will be obvious that certain changes and modifications may be practiced within the scope of the appended claims.

What is claimed is:

1. An improved method for transforming a digital data transfer file comprising a data set representing the image of a long bone to a robotic coordinate system of the type wherein preselected coordinates of the bone image are registered with corresponding coordinates of the actual bone immobilized in the robotic system, wherein the improvement comprises:
   registering between the robotic coordinate system and the image data set contained in the digital data transfer file (1) directional coordinates representing the bone axis and (2) at least one positional coordinate on the bone surface.

2. An improved method as in claim 1, wherein the directional coordinates represent the medullary canal of the bone and the positional coordinate is on a surface of the bone.

3. An improved method as in claim 1, further comprising registering a plurality of positional coordinates on the surface of the bone.

4. An improved method as in claim 1, wherein the long bone is a femur and the surface is in the region of the proximal calcar.

5. An improved method as in claim 1, wherein the positional coordinate is defined by an implanted marker.

6. A method for registering an image of a long bone with the bone immobilized in a system having a mechanical manipulator having an effector positionable in a coordinate system, wherein the method comprises:
   translating the effector axially through the medullary canal of the bone to acquire and store axial coordinates;
   positioning the effector at at least one external surface position on the bone to acquire at least one positional coordinate; and
   transforming a data set contained in a data transfer file representing an image of the bone to the coordinate system by registering the stored axial and positional coordinates of the bone with corresponding coordinates in the image data set.

7. A method as in claim 6, wherein the effector is centered within the medullary canal when the axial coordinates are acquired.

8. A method as in claim 7, wherein the effector is centered by inflating a centering balloon on the effector at the time each axial coordinate is acquired.

9. A method as in claim 6, wherein the effector is positioned at a plurality of surface positions on the bone.

10. A method as in claim 9, wherein the bone is a femur and the plurality of surface positions are in the outer cortex of the proximal calcar region.

11. A method as in claim 6, wherein the positional coordinate is defined by one or more markers implanted in the bone.

12. A method as in claim 11, wherein the bone is a femur and the marker is implanted in the proximal femur.

13. A method as in claim 6, wherein the transforming step comprises generating a transform function which can transform image data into the coordinate system of the manipulator system.

14. A method as in claim 6, further comprising obtaining the image data set.

15. A method as in claim 4, wherein the image data set is obtained by:
    providing a raw image data set of the bone;
    selecting and marking a plurality of coordinates along a centerline through the medullary canal; and
    generating a surface model representing a region near one end of the bone.

16. A method as in claim 15, wherein the bone is a femur and the surface model represents a surface in the outer cortex in the proximal calcar region.

17. A method for positioning a movable effector relative to a long bone immobilized in an operative space, said method comprising:
    providing an image data set of the bone which includes axial information and surface information:
    forming an access hole in the medullary cavity from a proximal end of the bone;
    immobilizing the bone in the operative space;
    translating the effector axially through the medullary cavity of the long bone;
    storing in a system data set axial positional information of the effector at at least two axially spaced-apart locations along the center line of the medullary cavity;
    positioning the effector against the surface of the bone;
    storing in the system data set surface positional information of the effector when contacting the surface;
    comparing the axial and surface information in the image data set with the axial and surface positional information stored in the system data set to generate a transform function; and
    positioning the effector relative to the bone using the transfer function based on in the image data set.

18. A method as in claim 17, wherein the effector is centered within the medullary canal when the positional information along the access hole is stored.

19. A method as in claim 18, wherein the effector is centered by inflating a centering balloon on the effector at the time each axial coordinate is acquired.

20. A method as in claim 17, wherein the effector is positioned at a plurality of surface positions on the bone.

21. A method as in claim 20, wherein the bone is a femur and the plurality of surface positions are in the outer cortex of the proximal calcar region.

22. A method as in claim 17, wherein the surface positional coordinate is defined by markers implanted in the bone.

23. A method as in claim 22, wherein the bone is a femur and the marker is implanted in the proximal calcar region.

24. A method as in claim 17, further comprising:
    providing a robotic system comprising (a) a manipulatable arm that carries the effector, (b) a bone fixator which is fixed relative to the manipulator arm and the operative space; and (c) a system controller;
    wherein the bone is immobilized in the bone fixator.

25. A method as in claim 24, wherein the controller positions the effector by moving the manipulatable arm.

26. A method as in claim 24, wherein the image data set and the system data set are maintained in the system controller.

27. An improved method for performing hip replacement surgery, said method being of the type wherein an image of the femur is used to control a robotic system to machine a cavity in the femoral canal to receive prosthetic implant and wherein an image data set is transformed to a coordinate system of the robotic system by registering preselected coordinates of the image data set with corresponding coordinates of the actual bone immobilized in the robotic system, wherein the improvement comprises:

registering between the robotic coordinate system and the image data set (1) directional coordinates representing the bone axis and (2) at least one positional coordinate on the bone surface.

28. An improved method as in claim 27, wherein the directional coordinates represent a line through the medullary canal of the bone and the positional coordinate is on a surface of the bone.

29. An improved method as in claim 27, further comprising registering a plurality of positional coordinates on the surface of the bone.

30. An improved method as in claim 27, wherein the long bone is a femur and the surface is in the region of the proximal calcar.

31. An improved method as in claim 27, wherein the positional coordinate is defined by an implanted marker.

32. An improved robotic system of the type having a manipulatable arm which carries a surgical cutter and a programmable controller which positions the cutter within a robotic coordinate system, wherein an image data set representing the image of a long bone is transformed to the robotic coordinate system, wherein the improvement comprises:

a controller program which transforms the image data set to the robotic coordinate system by registering (1) directional coordinates representing the bone axis and (2) at least one positional coordinate on the bone surface.

33. An improved robotic system in claim 32, wherein the directional coordinates represent a line through the medullary canal of the bone and the positional coordinate is on a surface of the bone.

34. An improved robotic system as in claim 32, wherein the controller program registers a plurality of positional coordinates on the surface of the bone.

35. An improved robotic system as in claim 32, wherein the long bone is a femur and the surface is in the region of the proximal calcar.

36. An improved robotic system as in claim 32, wherein the positional coordinate is defined by an implanted marker.

* * * * *